United States Patent [19]

Durden, Jr. et al.

[11] 3,956,500

[45] May 11, 1976

[54] CARBAMATE PESTICIDAL COMPOSITIONS

[75] Inventors: John A. Durden, Jr., South Charleston; Arthur P. Kurtz, Charleston, both of W. Va.

[73] Assignee: Union Carbide Corporation, New York, N.Y.

[22] Filed: Apr. 3, 1973

[21] Appl. No.: 347,446

[52] U.S. Cl. .......................... 424/276; 260/327 M; 260/327 P; 424/DIG. 8; 424/DIG. 10

[51] Int. Cl.$^2$ ...................... A01N 9/00; A01N 9/12

[58] Field of Search ............... 424/276, 277, DIG. 8

[56] References Cited

UNITED STATES PATENTS

| | | | |
|---|---|---|---|
| 3,183,148 | 5/1965 | Cannon et al. | 424/277 |
| 3,193,561 | 7/1965 | Addor | 424/277 |
| 3,338,782 | 8/1967 | Addor | 424/277 |
| 3,365,361 | 1/1968 | Addor | 424/277 |

*Primary Examiner*—V. D. Turner
*Attorney, Agent, or Firm*—Robert C. Brown

[57] ABSTRACT

Novel 1,3-oxathiolane and 1,4-oxathiane carbamoyloximes have been found to have exceptional miticidal, insecticidal and nematocidal activity.

28 Claims, No Drawings

CARBAMATE PESTICIDAL COMPOSITIONS

This invention relates to methods and compositions for combating insects, mites and nematodes.

The compounds which are employed as the active ingredients in the pesticidal compositions of this invention are new compounds corresponding to the following general formula:

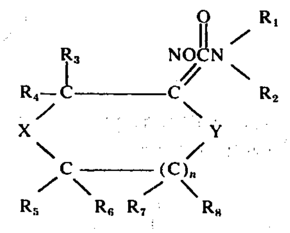

wherein:

$R_1$ and $R_2$ may be the same or different and may be hydrogen, lower alkyl, halogen substituted lower alkyl, cycloalkyl, lower alkoxyalkyl, lower alkylthioalkyl, lower alkylsulfinylalkyl, lower alkylsulfonylalkyl, lower alkenyl, lower alkynyl, aryl, aryl substituted with one or more halogen, lower alkyl or lower alkoxy substituents, lower alkanoyl, alkoxy or halogen substituted lower alkanesulfenyl, with the proviso that when $R_1$ is lower alkoxy, lower alkanoyl or halogen substituted lower alkanesulfenyl, $R_2$ is hydrogen or lower alkyl;

$R_3$, $R_4$, $R_5$, $R_6$, $R_7$ and $R_8$ may be the same or different and may be hydrogen, alkyl, alkenyl, alkoxyalkyl, alkylthioalkyl, alkylsulfinylalkyl or alkylsulfonylalkyl, with the proviso that no one substituent group may contain more than six carbon atoms;

X and Y may be O, S, SO or $SO_2$ with the proviso that X or Y is O and when X is O, Y is other than O and when Y is O, X is other than O; and

*n* is 0 or 1.

It will be appreciated that the new compositions of this invention will exist in at least two isomeric forms. In the "syn" configuration, the oxygen atom of the oximino function is on the same side of the oximino double bond as the Y heteroatom in the generic formula set forth above while in the "anti" configuration, the oxygen atom is on the opposite side of the oximino function. Both isomers are within the scope of our invention, however, the syn isomers are preferred due to their greater biological activity.

These compositions with varying degrees of efficacy are useful in combatting insects, mites and nematodes. In general, the compositions having the greatest degree of pesticidal activity are those in which the combined total number of carbon atoms in $R_3$, $R_4$, $R_5$, $R_6$, $R_7$ and $R_8$ substituents does not exceed about ten carbon atoms.

The new compositions of this invention can be prepared conveniently in accordance with the following general reaction scheme:

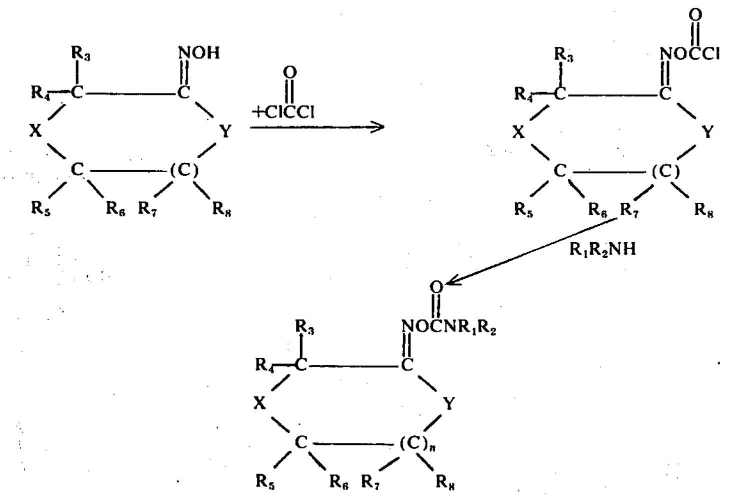

where $R_1$, $R_2$, $R_3$, $R_4$, $R_5$, $R_6$, $R_7$, $R_8$, X, Y and *n* are as described above.

The compositions of this invention where $R_1$ is hydrogen can be prepared by reacting the appropriate oxime precursor with an isocyanate in accordance with the following general reaction scheme:

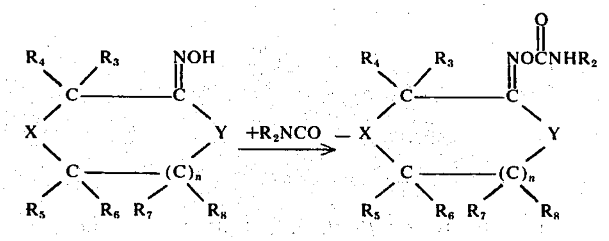

where $R_2$, $R_3$, $R_4$, $R_5$, $R_6$, $R_7$, $R_8$, X, Y and *n* are as defined above.

The compositions of this invention may also be prepared by reacting an appropriately substituted carbamoyl halide composition with an oximino oxathiolane or oxathiane composition.

The compositions of this invention wherein X or Y is SO or $SO_2$ can be prepared conveniently by selective oxidation of the corresponding oxathiane or oxathiolane composition with peracetic acid. In a like manner compounds in which any of $R_1$ through $R_8$ is lower alkylsulfinylalkyl or lower alkylsulfonylalkyl can be prepared by oxidation of the corresponding lower alkylthioalkyl function at an appropriate point in the synthetic procedure leading to that compound.

The compositions of this invention where $R_2$ is alkanoyl can be prepared conveniently by reacting a corresponding carbamoyloximino compound wherein $R_2$ is hydrogen with an alkanoic acid halide or anhydride.

The oxime precursor compounds can be prepared in a variety of ways including the syntheses illustrated by the following general reaction schemes leading to the oxathiolane precursor:

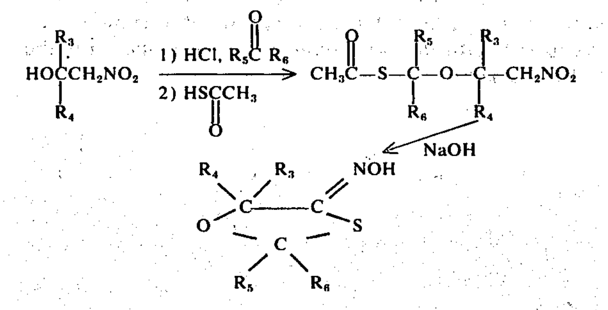

Alternatively, oxathiolane precursors can be prepared as follows:

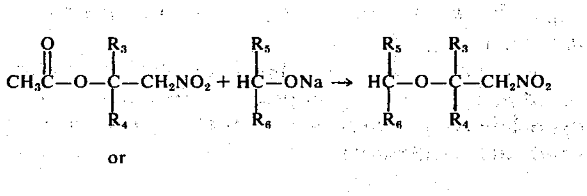

or

-continued

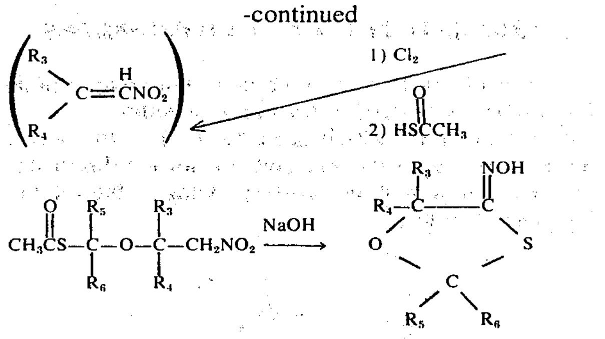

The 3-oximino-1,4-oxathiane precursors can be prepared by the following method:

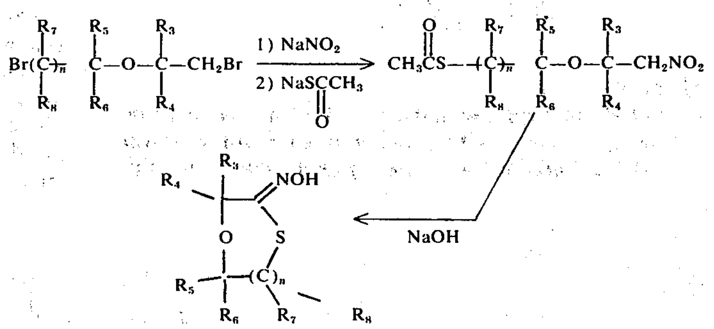

The 3-oximino-1,4-oxathiane precursors may also be prepared in the following manner:

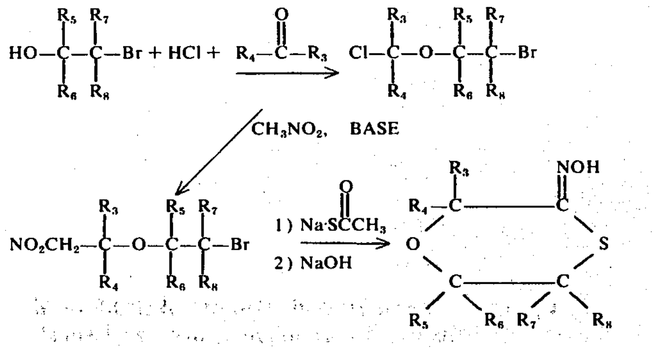

The 2-oximino-1,4-oxathiane and precursors can be prepared by the following method:

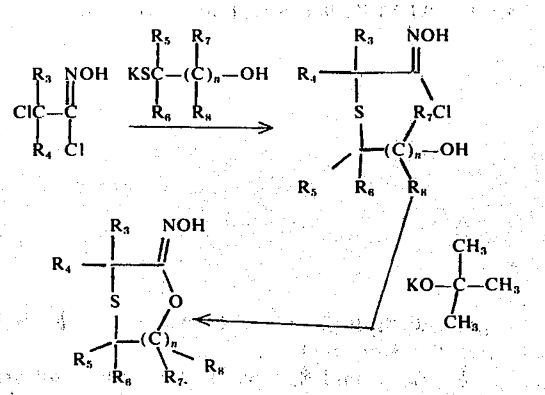

In each of the above general reaction schemes $R_3$, $R_4$, $R_5$, $R_6$, $R_7$, $R_8$ and n are as defined above.

The following specific examples are provided to more particularly illustrate the manner in which the new compositions of this invention may be prepared.

EXAMPLE I

PREPARATION OF 4-(METHYLCARBAMOYLOXIMINO)-1,3-OXATHIOLANE (Syn and Anti Forms)

A. Dry hydrogen chloride was bubbled through a slurry of 50 grams of 2-nitroethanol, 16.5 grams of paraformaldehyde, and 15.2 grams of calcium chloride which was stirred cooled at 0°–10° in an ice bath. When excess (over one equivalent) had been adsorbed, the cold mixture was filtered. Distillation in vacuo afforded 2-chloromethoxy-1-nitroethane, bp 72° (0.1 mm).

Analysis: Calc'd for $C_3H_6ClNO_3$: C, 25.82; H, 4.30; Cl, 25.39; N, 10.04. Found: C, 26.26; H, 4.60; Cl, 24.42; N, 9.80.

B. Thiolacetic acid (22.8 grams) and 41.7 grams of 2-chloromethoxy-1-nitroethane were mixed into 100 cc of tetrahydrofuran at room temperature and the clear solution was heated at reflux for 2 hours. The solution was cooled and 25 grams of pyridine was added. After an additional period of two hours at reflux the mixture was filtered and the solvent was removed from the filtrate by flash evaporation. The residue was taken up in ether, washed with 5 percent aqueous hydrochloric acid and water, dried over magnesium sulfate and the solvent again evaporated. Distillation in vacuo afforded 24.7 g of 2-acetylthiomethoxy-1-nitroethane, bp 106°–109° (0.2–0.5 mm); structure was confirmed by spectral analysis.

C. 171 Ml of 1.68N ethanolic sodium hydroxide and an equal volume of toluene were stirred vigorously at room temperature and a solution of 25.8 grams of the thioacetate were dissolved in 25 ml of toluene and dripped in over one hour (slightly exothermic). After stirring at room temperature for three hours, the mixture was diluted with water and ether, and 50 percent aqueous hydrochloric acid was added to pH = 4. The organic phase was separated and the aqueous phase extracted with a second portion of ether. Both organic solutions were washed with brine containing 5 percent aqueous sodium bicarbonate, dried over magnesium sulfate, and evaporated to give 16.5 grams of crude 4-oximino-1,3-oxathiolane. Recrystallization from toluene afforded pure oxime, 10.1 g, mp 88.0°–89.5°; structure confirmed by spectral analysis.

Analysis Calc'd for $C_3H_5NO_2S$: C, 30.25; H, 4.20; N, 11.76; S, 26.9. Found: C, 30.22; H, 4.50; N, 11.59; S, 27.1.

D. A 5.78 g quantity of the oxime was charged to a pressure bottle with 7.5 ml of methyl isocyanate, 4 drops of dibutyltin diacetate, and 150 ml of ethyl ether. After standing over the weekend crystals had deposited in the bottom of the reactor. Recrystallization from 5/1 isopropyl ether/ethylacetate afforded pure 4-(methylcarbamoyloximino)-1,3-oxathiolane (syn isomer), mp 100.1°–101.5°; structure confirmed by IR and nmr.

Analysis Calc'd for $C_5H_8N_2O_3S$: C, 34.08; H, 4.57; N, 15.89; S, 18.19. Found: C, 34.03; H, 4.94; N, 15.82; S, 18.1.

The anti isomer was isolated by dry-column chromatography (Silica Gel G, 30 percent ethyl acetate, 70 percent benzene) of mother liquors from the recrystallization. It had mp 138°–140°; nmr and IR confirmed structure and freedom from contamination with syn isomer.

High resolution mass measurement: Theory: 176.0255597; Observed: 176.025514.

EXAMPLE II

PREPARATION OF 4-(METHYLCARBAMOYLOXIMINO)-2-METHYL-1,3-OXATHIOLANE (Syn and Anti Forms)

A. 50.0 Grams of 2-nitroethanol was chloroalkylated with 26.5 grams of acetaldehyde and excess hydrogen chloride according to the procedure of Example I. The crude chloroalkyl ether resulting was reacted with 49 grams of thiolacetic acid and then 48 ml of pyridine and distilled in vacuo to give a fraction having bp 91°–94° (0.03 mm). This fraction, 24.1 grams, was about 75 percent 2-nitroethyl-1'-acetylthioethyl ether and was used without further purification in the next synthetic step. B. A quantity of 23.0 grams of the thiolacetate derivative was caused to react with 142 ml of 1.68N sodium hydroxide in absolute ethanol in 142 ml of toluene at room temperature for sixteen hours. Conventional workup afforded 13 grams of a dark oil, crude 4-oximino-2-methyl-1,3-oxathiolane. Analysis indicated the crude product to consist of a mixture of syn and anti isomers and about 10 percent unknown impurities. Attempts at purification by recrystallization failed; the isomers were resolved as carbamates.

C. A quantity of 8.0 grams of the crude oxime was caused to react with 8.0 ml of methyl isocyanate in the presence of dibutyltin diacetate in ethyl ether to give 8.3 grams of crude 4-(methylcarbamoyloximino)-2-methyl-1,3-oxathiolane. This crude product contained a predominance of anti isomer. Repeated recrystallization from isopropyl ether/ethyl acetate mixtures afforded pure anti isomer, mp (decomposing) 128°–137°. Isomeric purity of greater than 95 percent was confirmed.

Analysis Calc'd for $C_4H_7NO_2S$: C, 37.87; H, 5.30; N, 14.7; S, 16.9. Found: C, 37.61; H, 5.08; N, 14.6; S, 17.2.

D. The syn isomer could not be readily recovered from the mother liquors without anti isomer contamination. Carbamoylation of 5.0 grams crude oxime with methyl isocyanate in acetonitrile in the presence of triethylamine, however, afforded crude 4-(methylcarbamoyloximino)-2-methyl-1,3-oxathiolane in which the syn isomer predominated. Repeated recrystallization from isopropyl ether/ethyl acetate mixtures afforded pure syn isomer, mp 77°–79°.

Analysis Calc'd for $C_6H_{10}N_2O_3S$: C, 37.87; H, 5.30; N, 14.7; S, 16.9. Found: C, 37.7; H, 5.08; N, 14.7; S, 17.3.

EXAMPLE III

PREPARATION OF 4-(METHYLCARBAMOYLOXIMINO)-5-METHYL-1,3-OXATHIOLANE

A. A quantity of 206 grams of 1-nitro-2-propanol was chloromethylated with 60 grams paraformaldehyde and excess hydrogen chloride according to the procedure given in Example I. The crude chloromethylether resulting was reacted with 154 grams of thiolacetic acid and then 154 grams of pyridine and distilled in vacuo after workup as described in Example I to give 123 grams of 1-nitro-2-acetylthiomethyloxy propane; structure confirmed by spectral analysis.

Analysis Calc'd for $C_6H_{11}NO_4S$: C, 37.3; H, 5.74; N, 7.25. Found: C, 37.58; H, 5.59; N, 6.56.

B. A quantity of 131 grams of 1-nitro-2-acetylthiomethyloxy propane was caused to react with 835 ml of a solution of ethanolic 1.68 N sodium hydroxide in 830 ml of toluene at room temperature for sixteen hours. Workup as described in Example I and recrystallization from toluene afforded 50 grams of 4-oximino-5-methyl-1,3-oxathiolane, mp 80.5°–81.5°, 100% syn isomer by NMR analysis.

Analysis Calc'd for $C_4H_7NO_2S$: C, 36.07; H, 5.30; N, 10.52; S, 24.07. Found: C, 36.3; H, 5.12; N, 10.40; S, 24.13.

C. A quantity of 4.3 grams of 4-oximino-5-methyl-1,3-oxathiolane was caused to react with 3.5 ml of methylisocyanate in the presence of dibutyltin diacetate in ethyl ether and worked up as described in Example I to give 6 grams of crude 4-(methylcarbamoyloximino)-5-methyl-1,3-oxathiolane. Recrystallization from isopropyl ether/ethyl acetate afforded pure syn isomer, mp 70.0°–71.5°; structure confirmed by spectral analysis.

Analysis Calc'd for $C_6H_{10}N_2O_3S$: C, 37.87; H, 5.30; N, 14.73; S, 16.86. Found: C, 37.64; H, 5.02 N, 14.6; S, 16.61.

EXAMPLE IV

PREPARATION OF 4-(METHYLCARBAMOYLOXIMINO)-2-PROPYL-5-METHYL-1,3-OXATHIOLANE (CIS AND TRANS ISOMERS)

A. 1-Methyl-2-nitroethyl-1'-acetylthiobutyl ether was prepared using procedures similar to those described in Examples I and II by chloroalkylation of 1-nitro-2-propanol with n-butyraldehyde and hydrogen chloride followed by treatment of the intermediate chlorobutyl ether with thiolacetic acid and then pyridine. Treatment of this nitroalkylacylthio ether in toluene with ethanolic sodium hydroxide as described in Example I afforded crude 4- oximino-2-propyl-5-methyl-1,3-oxathiolane comprised of a mixture of Isomer A (NMR data suggests Trans Isomer) and Isomer B (NMR suggests Cis). Trituration of 26 grams of the crude oxime mixture with 150 ml of hexane and filtration afforded 3.0 grams pure Isomer A, mp 86°–88°.

Analysis Calc'd for $C_7H_{13}NO_2S$: C, 47.98; H, 7.48; N, 7.99. Found: C, 47.55; H, 7.61; N, 7.93.

A second crop, 4.0 grams, mp 80.5°–84°; analyzed (nmr) for 90 percent A/10 percent B. Evaporation of the mother liquors gave an oil, 17.5 grams, 20 percent A/80 percent B by nmr. Since this sample (in which isomer B predominated) could not be further purified by direct recrystallization, it was derivatized for further purification from non-oxime impurities. A quantity of 17 grams of the crude oxime sample containing predominantly isomer B was reacted with 30 ml of trimethylchlorosilane by stirring in 100 ml of pyridine at 10° for 30 minutes and then approximately 18 hours at room temperature. Filtration of pyridinium chloride, evaporation, dissolution in anhydrous ether, drying over magnesium sulfate filtration, a second solvent evaporation and distillation in vacuo afforded approximately 9 grams of 4-(trimethylsilyloximino)-2-propyl-5-methyl-1,3-oxathiolane, bp 61°–63° (0.1 mm), comprised of 15 percent Isomer A and 85 percent Isomer B.

Analysis Calc'd for $C_{10}H_{21}NO_2SSi$: C, 48.54; H, 8.55; N, 5.66. Found: C, 48.6; H, 8.31; N, 5.33.

The trimethylsilyl ether was quantitatively cleaved by mixing with small increments of water in stirring ethanol/tetrahydrofuran for 18 hours at room temperature. Evaporation of the solvents, dissolution in ether, rinsing with brine, drying over magnesium sulfate, filtration and evaporation afforded 5.7 grams of an oil, nearly pure oxime (mixture), isomer ratio unchanged from that of the trimethylsilyl ether.

B. Both the Isomer A oxime and (separately) the predominantly Isomer B oxime samples were converted to the corresponding methyl carbamates by reaction with methyl isocyanate in ether in the presence of dibutyltin diacetate as described in Example I. Recrystallization of both products from isopropyl ether afforded, in one instance, pure Isomer A (nmr suggests A is trans), mp 88.5°–89.0°, and in the other instance, pure Isomer B (nmr suggests cis), mp 59°–61°.

Analysis Calc'd for $C_9H_{16}N_2O_3S$: C, 46.53; H, 6.94; N, 12.06; S, 13.80. Found for A: C, 46.7; H, 6.93; N, 12.0; S, 14.52. Found for B: C, 46.3; H, 6.87; N, 11.9; S, 13.87.

EXAMPLE V

PREPARATION OF 4-(METHYLCARBAMOYLOXIMINO)-5-METHOXYMETHYL-1,3-OXATHIOLANE

A. Anhydrous methoxyacetaldehyde was obtained from the commercially available aqueous solution (77% methoxyacetaldehyde) by azeotropic distillation of the water with added chloroform followed by distillation of the anhydrous material (bp 85°–89°, 1ATM). The aldehyde used in the following preparation contained about 50 weight % chloroform from this process.

A stirring mixture of 51 grams of chloroform-contaminated methoxyacetaldehyde, 4.0 grams of potassium fluoride and 210 ml of isopropyl alcohol was brought to 30° in a reactor protected with a drying tube. A quantity of 73 grams of nitromethane was dripped in over a 30 minute period (mild exotherm to 37°). After stirring at ambient temperatures for 20 hours, the resulting solution was filtered and concentrated using a rotary evaporator. The resulting residue was dissolved in 150 ml of ethyl acetate and washed with 50 ml of water and 50 ml of saturated brine to which had been added 15 ml of 10% aqueous hydrochloric acid. After backextraction of both wash solutions with three 150 ml portions of ethyl acetate, the organic solutions were combined, dried over magnesium sulfate, filtered and the solvent removed by rotary evaporation. Distillation of the resulting residue gave 39 grams of 1-nitro-3-methoxypropan-2-ol, bp 78°–100° (0.025 mm Hg.); spectral data confirmed the desired structure.

Analysis Calc'd for: $C_4H_9NO_4$: C, 35,55; H, 6.71; N, 10.36. Found: C, 35.2; H, 6.88; N, 9.97.

B. A quantity of 38.5 grams of 1-nitro-3-methoxypropan-2-ol was chloromethylated with 8.53 grams paraformaldehyde and excess hydrogen chloride in a manner similar to that described in Example I. In this case, hydrogen chloride was passed through the reaction mixture at 0° for 15 hours after 1 equivalent had been absorbed. The resulting crude chloromethyl ether was then dissolved in tetrahydrofuran and reacted with 23.6 grams of thiolacetic acid and, subsequently, 22.5 ml of pyridine in a manner similar to the procedure given in Example I. After workup similar to that given in I, the crude thiolacetate was heated at 0.1 mm Hg until all volatiles having bp less than 100° had distilled off. A quantity of 14 grams of the resulting residue was reacted with 75 ml of a solution of ethanolic 1.68 N sodium hydroxide in 75 ml of toluene at room temperature for 16 hours. After workup as given in Example I, 7.1 gram of the crude product oxime was trimethylsilated with 9.0 grams of rimethylchlorosilane and pyridine in ether in a manner similar to that described in Example IV, and distilled in vacuo to give the oximetrimethylsilyl ether, bp 98°–104° (0.15 mm), 2.5 g, 70% desired product. Cleavage of the ether according to the method given in Example IV and recrystallization of the crude oxime product from toluene/hexane/isopropyl ether afforded pure 90.5°about 1 gram, mp 89.0°–5°C; structure confirmed by spectral analysis.

Analysis Calc'd for $C_5H_9NO_3S$: C, 36.80; H, 5.56; N, 8.58. Found: C, 36.9; H, 5.48; N, 8.36.

C. A quantity of 0.8 grams of the oxime described in B, was caused to react with 1 ml of methyl isocyanate in the presence of a catalytic amount of triethylamine in acetonitrile. After conventional workup, recrystallization from ethyl acetate/isopropyl ether afforded pure 4-(methylcarbamoyloximino)-5-methoxymethyl-1,3-oxathiolane, 0.6 gram, mp 105°–106.5°; structure confirmed by spectral analysis.

Analysis Calc'd for $C_7H_{12}N_2O_4S$: C, 38.17; H, 5.49; N, 12.72. Found: C, 37.9; H, 5.57; N, 12.7.

EXAMPLE VI

PREPARATION OF 4-(N-METHYL-N-ACETYLCARBAMOYLOXIMINO)-5-METHYL-1,3-OXATHIOLANE 2.0 Grams of 4(methylcarbamoyloximino)-5-methyl-1,3-oxathiolane was dissolved in 20 ml of ethyl acetate in a stirred reaction vessel at room temperature. After the addition of 3 ml of acetic anhydride, a solution of 1 drop concentrated sulfuric acid in 5 ml of ethyl acetate was added. After stirring the clear solution containing 1 drop of concentrated sulfuric acid in 5 ml of powdered sodium bicarbonate was added and the heterogeneous mixture was stirred for 5 minutes. The solids were removed by filtration, 30 ml of hexane were added to the filtrate, and the resulting solution cooled at −10° for several hours. Filtration afforded crude 4-(N-methyl-N-acetyl-carbamoyloximino)-5-methyl-1,3-oxathiolane which on recrystallization from 2/1 isopropyl ether/ethyl acetate had mp 109°–110°.

Analysis Calc'd for $C_8H_{12}N_2O_4S$: C, 41.37; H, 5.21; N, 12.06. Found: C, 41.1; H, 5.35; N, 11.9.

EXAMPLE VII

PREPARATION OF 4-(N-METHYL-N-TRICHLOROMETHANESULFENYLCARBAMOYLOXIMINO)-5-METHYL-1,3-OXATHIOLANE

A. methylcarbamoyl fluoride was prepared according to the procedure of G. D. Buckley, H. A. Piggott and A. J. E. Welch, *J. Chem. Soc.*, 864 (1945).

B. N-Methyl-N-trichloromethanesulfenylcarbamoyl fluoride was prepared from methylcarbamoyl fluoride and trichloromethanesulfenyl chloride according to the method reported in West Germany Pat. No. 1.297,095 (Farbenfabriken Bayer, A. G), June 12, 1969.

C. A quantity of 1 gram of 4-(oximino)-5-methyl-1,3-oxathiolane was caused to react with 2 grams of N-methyl-N-trichloromethanesulfenylcarbamoyl fluoride in 50 ml of tetrahydrofuran in the presence of 1.05 ml of triethylamine at room temperature for 1.5 hours in a manner similar to the method reported in Belgium Pat. No. 765,514 (Farbenfabriken Bayer, A. G.), Aug. 10, 1971. The reaction mixture was concentrated by evaporation, redissolved in ethyl acetate, and the solution washed with water and saturated brine, dried over magnesium sulfate, filtered, and evaporated. The oily product was purified by preparative thin-layer chromatography (silica gel, 10 percent ethyl acetate/benzene) yielding pure 4-(N-methyl-N-trichloromethanesulfenylcarbamoyloximino)-5-methyl-1,3-oxathiolane, mp 58.0°–60.0°.

Analysis Calc'd for $C_7H_9Cl_3N_2O_3S_2$: C, 24.76; H, 2.67; N, 8.24; Found: C, 25.3; H, 2.75; N, 8.34.

EXAMPLE VIII

PREPARATION OF 4-(METHOXYMETHYLCARBAMOYLOXIMINO)-5-METHYL-1,3-OXATHIOLANE

A quantity of 5 ml of methoxymethyl isocyanate was caused to react with 5 grams of 4-oximino-5-methyl-1,3-oxathiolane dissolved in 100 ml of anhydrous ether containing 10 drops of triethylamine over a period of 48 hours at room temperature. Conventional workup and recrystallization from isopropyl ether/ethyl acetate afforded 5.5 grams of product, mp 78°–79°; structure confirmed by spectral analysis.

Analysis Calc'd for $C_7H_{12}N_2O_4S$: C, 38.17; H, 5.49; N, 12.71; S, 14.56. Found: C, 38.3; H, 5.35; N, 12.6; S, 14.76.

EXAMPLE IX

PREPARATION OF 4-(ALLYLCARBAMOYLOXIMINO)-5-METHYL-1,3-OXATHIOLANE

A quantity of 3 ml of allyl isocyanate was caused to react with 3 grams of 4-oximino-5-methyl-1,3-oxathiolane dissolved in 50 ml of ether containing 2 drops of triethylamine over a period of 20 hours at room temperature. Conventional workup and recrystallization from isopropyl ether afforded 3 grams of product, mp 66.0°–67.5°, structure confirmed by spectral analysis.

Analysis Calc'd for $C_8H_{12}N_2O_3S$: C, 44.43; H, 5.59; N, 12.95. Found: C, 44.2; H, 5.55; N, 12.8.

EXAMPLE X

PREPARATION OF 4-[N-(2′,4′-DIMETHYLPHENYL)CARBAMOYLOXIMINO]-1,3-OXATHIOLANE

A quantity of 5.0 ml of 2,4-dimethylphenyl isocyanate was caused to react with 4 grams of 4-oximino-1,3-oxathiolane dissolved in 100 ml of anhydrous ether containing 3 drops of dibutyltin diacetate over 6 days at room temperature. The crude product solid was separated by filtration and dissolved in 100 ml of isopropyl ether mixed with 100 ml of acetone. After removal of the solids precipitating at room temperature (about 1.0 gram, mp > 250°) the residue resulting from evaporation of the filtrate was recrystallized from a 2:1 ispropyl ether/ethyl acetate mixture yielding 3 grams of product, mp 124°–126°; structure confirmed by spectral analysis.

Analysis Calc'd for $C_{12}H_{14}N_2O_3S$: C, 54.12; H, 5.30; N, 10.52. Found: C, 54.2; H, 5.37 N, 10.4.

EXAMPLE XI

PREPARATION OF 4-(2-CHLOROETHYLCARBAMOYLOXIMINO)-5-METHYL-1,3-OXATHIOLANE

4-Oximino-5-methyl-1,3-oxathiolane was caused to react with 2-chloroethylisocyanate in the presence of dibutyltin diacetate in ether. The reaction mixture was worked up and recrystallized in the manner described in Example I. The product had a mp 88.5°–90.5°.

Analysis Calc'd for $C_7H_{11}ClN_2O_3S$: C, 35.22; H, 4.64; N, 11.73. Found: C, 35.1; H, 4.83; N, 11.6.

EXAMPLE XII

PREPARATION OF 4-(DIMETHYLCARBAMOYLOXIMINO)-1,3-OXATHIOLANE

A. A quantity of 6 grams of 4-oximino-1,3-oxathiolane dissolved in 100 ml of anhydrous ether was added over 30 minutes to a solution of 10 grams of phosgene in 100 ml of anhydrous ether maintained at −10°C. A quantity of 6 grams of N,N-dimethylaniline dissolved in 200 ml of anhydrous ether was then added dropwise to the cooled phosgene/oxime solution over a 30 minute period. The heterogeneous mixture was stirred at −10° for 2 hours, filtered in an inert atmosphere and the filtrate concentrated under a vacuum to about 250 ml. The concentrated solution was cooled to 10° in a stirring vessel, 12 ml of 40 percent aqueous dimethylamine was added dropwise, and the mixture stirred for 1 hour at 10°. A volume of 100 ml of water was added, the phases separated, and the organic phase washed with two 50 ml portions of saturated brine. The three aqueous solutions were extracted sequentially with a volume of 300 ml of ether. The combined ether solutions were dried over magnesium sulfate, filtered, and evaporated. Recrystallization of the crude 4-(dimethylcarbamoyloximino)-1,3-oxathiolane afforded pure product, mp 87.5°–88.0°.

Analysis Calc'd for $C_6H_{10}N_2O_3S$: C, 37.88; H, 5.30; N, 14.72; S, 16.85. Found: C, 38.0; H, 5.29; N, 14.4; S, 17.68.

EXAMPLE XIII

PREPARATION OF 4-(METHYLCARBAMOYLOXIMONO)-5-METHYL-1,3-OXATHIOLANE-3-OXIDE 13.7 Grams of a solution of peracetic acid (22.8 percent) in ethyl acetate was added over 1.5 hours to a stirring solution 7.65 grams 4-(methylcarbamoyloximino)-5-methyl-1,3-oxathiolane dissolved in 200 ml of ethyl acetate maintained at 0°–5°. The resulting clear solution was allowed to warm gradually to room temperature and to stand overnight. The solution was then washed with 50 ml of saturated aqueous sodium bicarbonate and 25 ml of saturated brine, dried over magnesium sulfate, filtered and evaporated. The thick oil resulting (5 grams of a mixture of starting material and product sulfoxide) was induced to crystallize by redissolving in 50 ml of ethyl acetate at room temperature and addition of hexane until just turbid. Recrystallization of the first crop, 1.9 grams, from 2/1 isopropyl ether afforded 4-(methylcarbamoyloximino)-5-methyl-1,3-oxathiolane-3-oxide, mp 115°–120°. The sulfoxide was free of contamination by either sulfide or sulfone. The broad melting point range and nmr spectrum confirmed the presence of two isomers (ring methyl cis to S=O; ring methyl trans to S=O).

Analysis Calc'd for $C_6H_{10}N_2O_4S$: C, 34.94; H, 4.88; N, 13.58; S, 5.55. Found: C, 34.8; H, 4.93; N, 13.4; S, 15.71.

EXAMPLE XIV

PREPARATION OF 4-(METHYLCARBAMOYLOXIMINO)-5-METHYL-1,3-OXATHIOLANE-3,3-DIOXIDE

3 Grams of 4-(methylcarbamoyloximino)-5-methyl-1,3-oxathiolane was treated with peracetic acid in a manner similar to that described in Example XIII but using increments of peracetic acid (22.8 percent in ethyl acetate) solution at varying temperatures and for varying time periods as follows: 12 grams (room temperature for 1 hour; 40° for 18 hours; room temperature for 30 hours); 8 grams (40° for 14 hours); 8 grams (40° for 24 hours). Workup as described in Example XIII afforded a thick oil (2.5 grams), 4-(methylcarbamoyloximino)-5-methyl-1,3-oxathiolane-3,3-dioxide. Thin-layer chromatography, IR, nmr, and elemental analyses confirmed the structure assignment and attested to freedom from contamination with starting material or sulfoxide. The product could not be induced to crystallize and, even after exposure to 0.01 mm vacuum for 24 hours at 35°, showed 10.6 mole percent contamination with ethyl acetate (nmr).

Analysis Calc'd for $C_6H_{10}N_2O_5S$ plus 10.6 mole percent EtOAc; C, 34.77; H, 5.02; N, 11.27. Found: C, 34.6; H, 4.98; N, 11.6.

EXAMPLE XV

PREPARATION OF 3-(METHYLCARBAMOYLOXIMINO)-1,4-OXATHIANE

A solution of 69 g of sodium nitrite in 500 ml of dimethylsulfoxide (DMSO) was added over a six-hour period to a stirred solution of 300 g of bis-2-bromoethyl ether in 1100 ml of DMSO. During the addition the reaction was mildly exothermic, and the temperature was maintained near 30° by intermittent ice-bath cooling. The resulting clear solution was allowed to stand at room temperature overnight, and the DMSO was "stripped" using a flash evaporator (60° bath, pressure 1–5 mm) until solids began to form in the evaporation flask. Addition of 1 liter of saturated brine afforded an orange oil and an aqueous solution. After separation, the aqueous phase was extracted with 5 portions of 500 ml ethyl acetate. The oil and ethyl acetate extracts were combined, dried over magnesium sulfate and evaporated, to yield 220 g of an orange oil. Infrared and TLC data indicated the crude product to be approximately a 50/50 mixture of starting material and the desired product, 2-(bromoethyloxy)-1-nitroethane. This mixture could not be fractionated by distillation in vacuo; an attempt resulted in strongly exothermic decomposition when the kettle was heated to 60°.

B. To a stirring solution of potassium thioacetate in aqueous ethanol (made by addition of 300 ml of ethanol to a solution of 101 g of potassium carbonate and 61 g of thioacetic acid in 120 ml of water) was added, over a two hour period at room temperature, 100 grams of the crude 2-(bromoethyloxy)-1-nitroethane described above. During the addition, the temperature was maintained at 25°–30° by intermittent cooling. After stirring overnight, salts were filtered, the filtrate was diluted with 1 liter of water and 500 ml of ether, and the phases separated. The aqueous phase was extracted with two 500 ml portions of ether. The combined organic materials were washed with water to which increments of hydrochloric acid were added until the pH remained less than 5, dried over magnesium sulfate, and evaporated. Distillation of the residue in vacuo afforded a fraction, bp 98°–103° (0.1 mm) which TLC; NMR and IR analysis showed to consist of 40 mole percent of the desired product contaminated with 60 mole percent of the bis-(2-acetylthio)-ethyl ether derived from the bis-bromo compound in the starting material. C. 230 Ml of 1.68N ethanolic sodium hydroxide, 300 ml of absolute ethanol and 400 ml of toluene were stirred vigorously at 55°–65° and a solution of 34.5 grams crude 2-(2-acetylthioethoxy)-1-nitroethane (contaminated with bis-(2-acetylthioethyl) ether) dissolved in 50 ml of toluene was added dropwise over one hour followed by stirring at 60° for an additional 2.5 hours and at room temperature for 16 hours. Conventional workup and recrystallization from toluene afforded pure 3-oximino-1,4-oxathiane, mp 105°–106.5°.

Analysis Calc'd for $C_4H_7NO_2S$: C, 36.08; H, 5.30; N, 10.53; S, 24.08. Found: C, 36.22; H, 5.25; N, 10.2; S, 24.16.

D. Carbamoylation of 3-oximino-1,4-oxathiane with methyl isocyanate according to the method described in Example I and recrystallization of the crude product from 10/1 isopropyl ether/ethyl acetate afforded pure 3-(methylcarbamoyloximino)-1,4-oxathiane, mp 102°–103°.

Analysis Calc'd for $C_6H_{10}N_2O_3S$: C, 37.87; H, 5.30; N, 14.73; S, 16.86. Found: C, 36.9; H, 4.79; N, 14.2; S, 16.7.

EXAMPLE XVI

PREPARATION OF 2-(METHYLCARBAMOYLOXIMINO)-3,3-DIMETHYL-1,4-OXATHIANE

A. A solution of the potassium salt of 2-mercaptoethanol in tert-butyl alcohol was prepared by adding 6 grams of 2-mercaptoethanol to a solution of 6.45 grams of potassium tert-butoxide in 100 ml of tert-butyl alcohol in an inert atmosphere. After stirring this solution 30 minutes at room temperature, it was added dropwise over a one hour period to a stirring solution of 10 grams of 2-chloro-2-methylpropionhydroxamoyl chloride in 100 ml of tert-butyl alcohol at ambient temperature under an inert atmosphere. The resulting mixture was stirred for 15 hours at ambient temperature, and then added dropwise over a two hour period to a stirring solution of 14.4 grams potassium tert-butoxide in 150 ml of tert-butyl alcohol. After stirring the resulting suspension for two hours at ambient temperature, the mixture was stirred at 50° for 48 hours. After cooling, the reaction mixture was neutralized with 10% aqueous hydrochloric acid and the whole added to a mixture of 150 ml of saturated brine and 500 ml of ethyl acetate. After equilibration and separation of phases, the aqueous phase was extracted with three portions of ethyl acetate. The combined organic phases were dried over magnesium sulfate, filtered, and the solvent was removed by evaporation yielding 11.5 grams of a reddish oil. This residue was extracted with three 50 ml portions of anhydrous ethyl ether. After evaporation of this extract to a residue, the latter was extracted with three 50 ml portions of isopropyl ether maintained at 20°. Evaporation of this extract gave 3.5 grams of crude oxime which could not be induced to crystallize. NMR and IR spectra confirmed the presence of about 70% desired oxime.

B. A quantity of 3.2 grams of crude 2-oximino-3,3-dimethyl-1,4-oxathiane was caused to react with 4 ml of methyl isocyanate in 75 ml of ether containing 5 drops of dibutyltin diacetate at room temperature for twenty hours. The excess methyl isocyanate and solvent were evaporated, and the residue taken up in ethyl acetate. After rinsing this solution with 100 ml of saturated brine and back-extraction with 100 ml of ethyl acetate, the combined organic solutions were dried over magnesium sulfate, filtered, and the solvent evaporated. The resulting thick oil was triturated with about 30 ml of a 3:1 isopropyl ether/ethyl acetate mixture at room temperature. Filtration afforded 0.7 g of pure 2-(methylcarbamoyloximino)-3,3-dimethyl-1,4-oxathiane, mp 67.0°–68.0°; structure confirmed by spectral analysis.

Analysis Calc'd for $C_9H_{14}N_2O_4S$: C, 43.89; H, 5.73; N, 11.37. Found: C, 43.8; H, 5.69; N, 11.3.

The following compositions in addition to those described in the above Examples are illustrative of the new compositions of this invention:

4-(methylcarbamoyloximino)-5,5-dimethyl-1,3-oxathiolane
4-(carbamoyloximino)-2-propenyl-1,3-oxathiolane
4-(methylcarbamoyloximino)-5,5-diethyl-1,3-oxathiolane
4-(dimethylcarbamoyloximino)-2-ethoxymethyl-1,3-oxathiolane
4-(chloroethylcarbamoyloximino)-2-(2-propylthioethyl)-1,3-oxathiolane
4-(methylcarbamoyloximino)-2,2-dimethyl-1,3-oxathiolane
4-(carbamoyloximino)-5-methyl-2-methylsulfinylethyl-1,3-oxathiolane
4-(ethylcarbamoyloximino)-5-(2-methylsulfonylethyl)-1,3-oxathiolane
4-(methylcarbamoyloximino)-2,2,5,5-tetramethyl-1,3-oxathiolane
4-(methylcarbamoyloximino)-2,5-bis-(2-methoxyethyl)-1,3-oxathiolane
4-(dimethylcarbamoyloximino)-5-(4-methylphenyl)-1,3-oxathiolane
4-(carbamoyloximino)-5-(2-ethylthioethyl)-1,3-oxathiolane
4-(methylcarbamoyloximino)-2-isobutyl-1,3-oxathiolane
4-(carbamoyloximino)-5-(2-isopropoxyethyl)-1,3-oxathiolane
4-(methylcarbamoyloximino)-2-amyl-1,3-oxathiolane
4-(methyloxycarbamoyloximino)-5-methyl-1,3-oxathiolane
4-(ethylthiomethylcarbamoyloximino)-5-methyl-1,3-oxathiolane
5-(methylcarbamoyl)-4-methyl-1,3-oxathiolane
5-(methylcarbamoyl)-4-methyl-1,3-oxathiolane-3-oxide
5-(methylcarbamoyl)-4-methyl-1,3-oxathiolane-3,3-dioxide
4-(ethylsulfinylmethylcarbamoyloximino)-5-methyl-1,3-oxathiolane 4-(ethylsulfonylmethylcarbamoyloximino)-5-methyl-1,3-oxathiolane-3-oxide
4-(propargylcarbamoyloximino)-5,5-dimethyl-1,3-oxathiolane
4-(propoxycarbamoyloximino)-2,2-dimethyl-1,3-oxathiolane
4-(cyclohexylcarbamoyloximino)-5-methyl-1,3-oxathiolane
4-(carbamoyloximino)-5-methylthiomethyl-1,3-oxathiolane
4-(2,4-dichlorophenylcarbamoyloximino)-5-methyl-1,3-oxathiolane
4-(methylcarbamoyloximino)-5-ethyl-1,3-oxathiolane-3,3-dioxide
4-(propylcarbamoyloximino)-2,2-dimethyl-1,3-oxathiolane
4-(carbamoyloximino)-5-t-butyl-1,3-oxathiolane
4(2-methylthioethylcarbamoyloximino)-5,5-dimethyl-1,3-oxathiolane
4-(N-acetylcarbamoyloximino)-1,3-oxathiolane
4-(N-acetylcarbamoyloximino)-5-methyl-1,3-oxathiolane
4-(carbamoyloximino)-5-ethyl-1,3-oxathiolane
4-(methylcarbamoyloximino)-5-methylsulfonylmethyl-1,3-oxathiolane-3,3-dioxide
4-(carbamoyloximino)-2,5-diethyl-1,3-oxathiolane
4-(N-methyl-N-tetrachloroethanesulfenylcarbamoyloximino)-5,5-dimethyl-1,3-oxathiolane
3-(methylcarbamoyloximino)-2-methyl-1,4-oxathiane
3-(N-methyl-N-trichloromethanesulfenylcarbamoyloximino)-2-methyl-1,4-oxathiane
3-(methylcarbamoyloximino)-2,2-dimethyl-1,4-oxathiane
3-(N-methyl-N-trichloromethanesulfenylcarbamoyloximino)-2,2-dimethyl-1,4-oxathiane
4-(N-methyl-N-propionylcarbamoyloximino)-2-butyl-1,3-oxathiolane
3-(methylcarbamoyloximino)-6,6-dimethyl-1,4-oxathiane
3-(carbamoyloximino)-2-methylsulfonylmethyl-1,4-oxathiane
3-(methylcarbamoyloximino)-1,4-oxathiane-4-oxide
3-(methylcarbamoyloximino)-2-propyl-1,4-oxathiane
3-(methylcarbamoyloximino)-5,6-dimethyl-1,4-oxathiane
3-(methylcarbamoyloximino)-1,4-oxathiane-4,4-dioxide
3-(carbamoyloximino)-2-t-butyl-1,4-oxathiane
3-(methylcarbamoyloximino)-2-(2-methoxyethyl)-1,4-oxathiane
3-(methylcarbamoyloximino)-2-(2-methoxyethyl)-1,4-oxathiane
2-(methylcarbamoyloximino)-3-isopropyl-1,4-oxathiane
2-(carbamoyloximino)-3,5,6-trimethyl-1,4-oxathiane
2-(methylcarbamoyloximino)-3-t-butyl-1,4-oxathiane
4-(N-methyl-N-trichloromethanesulfenylcarbamoyloximino)-5-ethyl-1,3-oxathiolane
4-(N-methyl-N-trichloromethanesulfenylcarbamoyloximino)-2,5-dimethyl-1,3-oxathiolane
4-(N-methyl-N-trichloromethanesulfenylcarbamoyloximino)-5,5-dimethyl-1,3-oxathiolane
4-(methylcarbamoyloximino)-5-(2-methylthioethyl)-1,3-oxathiolane
4-(methylcarbamoyloximino)-5-(2-methylsulfinylethyl)-1,3-oxathiolane
4-(methylcarbamoyloximino)-5-(2-methylsulfonylethyl)-1,3-oxathiolane 2-(methylcarbamoyloximino)-3,3-dimethyl-1,4-oxathiane-4-oxide
2-(methylcarbamoyloximino)-3,3-dimethyl-1,4-oxathiane-4,4-dioxide Selected species of the new compounds were evaluated to determine their pesticidal activity against mites, nematodes and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70°F. and 50–70 per cent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70°F. and 50–70 per cent, respectively. Aphids which fell onto the paper and were unable to remain standing after being uprighted were considered dead. Aphids remaining on the plants were observed closely for movement and those which were unable to move the length of the body upon stimulation by prodding were considered dead. Per cent mortality was recorded for various concentration levels.

Southern Armyworm Leaf Spray Test

Larvae of the southern armyworm (*Prodenia eridania*, (Cram.)), reared on Tendergreen bean plants at a emperature of 80°±5°F. and a relative humidity of 50±5 per cent, constituted the test insects.

The test compounds were formulated by diluting the stock suspension with water to give a suspension containing temperature 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85°F. for three days. Although the larvae could easily consume the whole leaf within twenty-four hours, no more food was added. Larvae which were unable to move the length of the body, even upon stimulation by prodding, were considered dead. Per cent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5°F. and 50±5 per cent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5°F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5°F. and 50±5 per cent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 per cent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for 24 hours, at a temperature of 80°±5°F. and the relative humidity of 50±5 per cent. Flies which showed no sign of movement on prodding were considered dead.

Mite Foliage Spray Test

Adults and numphal stages of the two-spotted mite (*Tetranychus urticae* Koch), reared on Tendergreen bean plants at 80±5 per cent relative humidity, were the test organisms. Infested leaves from a stock culture were placed on the primary leaves of two bean plants six to eight inches in height, growing in a 2½ inch clay pot. 150–300 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 per cent relative humidity for six days, after which a mortality count of motile forms was made. Microscopic examination for motile forms was made on the leaves of the test plants. Any individual which was capable of locomotion upon prodding was considered living.

Nematocide Test

The test organism used was the infective migratory larvae of the root-knot nematode, *Meloidogyne incognita* var. acrita, reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds against aphid, mite, Southern Armyworm, Bean Beetle and house fly was rated as follows:

A = no control
B = partial control
C = excellent control

In the test for activity against nematodes activity was rated as follows:

1 = severe galling, equal to untreated plants
2 = moderate galling
3 = light galling
4 = very light galling
5 = no galling, perfect control Dashes indicate no test conducted.

TABLE I

| Name | M.P. °C. | PEST<br>Aphid | Mite | Southern Army-worm | Bean Beetle | Housefly | Nema-tode |
|---|---|---|---|---|---|---|---|
| 4-(methylcarbamoyloximino)-1,3-oxathiolane (syn) | 100.0–101.5 | A | A | A | A | A | 4 |
| 4-(methylcarbamoyloximino)-1,3-oxathiolane (anti) | 138.0–140.0 | A | B | B | B | A | — |
| 4-(phenylcarbamoyloximino)-1,3-oxathiolane (syn) | 147.0–148.0 | C | C | C | C | C | 3 |
| 4-(2,4-dimethylphenyl-carbamoyloximino-1,3-oxathiolane (syn) | 124.0–126.0 | C | B | C | C | C | — |
| 4-(dimethylcarbamoyl-oximino)-1,3-oxathiolane (syn) | 87.5–88.0 | A | C | C | C | A | 1 |
| 4-(carbamoyloximino)-1,3-oxathiolane (syn) | 131.0–133.0 | 13 | C | C | C | A | 1 |
| 4-(2-chloroethylcarbamoyl-oximino)-1,3-oxathiolane (19% syn; 81% anti) | 77.5–83.0 | C | C | C | C | C | 1 |
| 4-(2-chloroethyl-carbamoyloximino)-1,3-oxathiolane (syn) | 100.0–101.0 | C | C | C | C | A | — |
| 4-(methylcarbamoyl-oximino)-5-methyl-1,3-oxathiolane (syn) | 70.0–71.5 | A | B | A | A | A | 3 |
| 4-(phenylcarbamoyl-oximino)-5-methyl-1,3-oxathiolane (syn) | 118.0–119.0 | — | C | C | B | C | 1 |
| 4-(dimethylcarbamoyl-oximino)-5-methyl-1,3-oxathiolane (syn) | 58–60 | A | B | C | B | A | — |
| 4-(carbamoyloximino)-5-methyl-1,3-oxathiolane (63% syn/37% anti) | * | A | A | A | A | A | — |
| 4-(2-chloroethylcarbamoyl-oximino)-5-methyl-1,3-oxathiolane (syn) | 88.5–90.5 | A | C | C | B | A | — |
| 4-(ethylcarbamoyloximino)-5-methyl-1,3-oxathiolane (syn) | 76.5–77.0 | A | B | A | A | A | 1 |
| 4-(allylcarbamoyl-oximino)-5-methyl-1,3-oxathiolane (syn) | 66.0–67.5 | A | B | B | A | A | 1 |
| 4-(methoxymethyl-carbamoyloximino)-5-methyl-1,3-oxathiolane (syn) | 78.0–79.0 | A | C | C | B | A | 1 |
| 4-(methylcarbamoyl-oximino)-5-methyl-1,3-oxathiolane-3-oxide (isomer mix (syn) | 115.0–120.0 | — | C | C | B | A | 1 |
| 4-(methylcarbamoyl-oximono)-5-methyl-1,3-oxathiolane-3,3-dioxide (syn) | ** | C | C | C | C | A | 1 |
| 4-(N-methyl-N-trichloro-methanesulfenylcarbamoyl-oximino)-5-methyl-1,3-oxathiolane (syn) | 58.0–60.0 | A | A | A | A | A | 3 |
| 4-(N-methyl-N-acetyl-carbamoyloximino)-5-methyl-1,3-oxathiolane (syn) | 109.0–110.0 | B | B | A | A | C | 1 |
| 4-(methylcarbamoyl-oximino)-2-methyl-1,3-oxathiolane (syn) | 77.0–79.0 | A | B | B | A | A | 1 |
| 4-(methylcarbamoyl-oximino)-2-methyl-1,3-oxathiolane (anti) | dec 128–137 | A | B | C | C | A | 1 |
| 4-(methylcarbamoyl-oximino)-2-ethyl-1,3-oxathiolane (syn) | 110.5–111.5 | A | B | B | B | A | 3 |
| 4-(methylcarbamoyl-oximino)-5-ethyl-1,3-oxathiolane (syn) | 63.0–65.0 | A | A | A | A | A | 3 |
| 4-(methylcarbamoyl-oximino)-5-propyl-1,3-oxathiolane (syn) | 65.0–66.0 | C | C | C | C | A | 1 |
| 4-(methylcarbamoyl-oximino)-5-propyl-1,3- | 90.0–91.5 | — | — | B | — | A | — |

-continued

TABLE I

| Name | M.P. °C. | PEST<br>Aphid | Mite | Southern Army-worm | Bean Beetle | Housefly | Nema-tode |
|---|---|---|---|---|---|---|---|
| oxathiolane (anti) | | | | | | | |
| 4-(carbamoyloximino)-5-propyl-1,3-oxathiolane (syn) | 96.0–96.5 | C | C | B | A | A | — |
| 4-(methylcarbamoyl-oximino)-5-isopropyl-1,3-oxathiolane (syn) | 71.0–73.0 | A | B | C | A | A | 1 |
| 4-(methylcarbamoyl-oximino)-5-(2-methoxy-ethyl)-1,3-oxathiolane (syn) | 94.8–96.0 | C | B | B | A | A | — |
| 4-(methylcarbamoyl-oximino)-5-methoxymethyl-1,3-oxathiolane (syn) | 105.5–106.5 | A | B | C | A | A | — |
| 4-(methylcarbamoyl-oximino)-2,5-dimethyl-1,3-oxathiolane (50/50 cis/trans; syn) | *** | A | A | A | A | A | 1 |
| 4-(ethylcarbamoyl-oximino)-2,5-dimethyl-1,3-oxathiolane (50/50 cis/trans; syn) | 64.0–70.0 | A | A | A | C | A | — |
| 4-(allylcarbamoyl-oximino)-2,5-dimethyl-1,3-oxathiolane (50/50 cis/trans; syn) | **** | A | A | C | C | A | — |
| 4-(methylcarbamoyl-oximino)-2-propyl-5-methyl-1,3-oxathiolane (Isomer A: syn) | 88.5–89.0 | A | C | C | A | A | 3 |
| 4-(methylcarbamoyl-oximino)-2-propyl-5-methyl-1,3-oxathiolane (Isomer B: syn) | 59.0–61.0 | A | B | C | A | A | 1 |
| 4-(methylcarbamoyl-oximino)-2-propyl-5-methyl-1,3-oxathiolane-3-oxide (mixed isomers: syn) | 103.5–110.5 | C | C | C | B | B | 1 |
| 3-(methylcarbamoyl-oximino)-1,4-oxathiane (syn) | 102–103 | B | B | A | A | A | 3 |
| 2-(methylcarbamoyl-oximino)-3,3-dimethyl-1,4-oxathiane | 67.0–68.0 | A | A | A | A | A | — |
| 4-(N-methyl-N-acetyl-carbamoyloximino)-1,3-oxathiolane | 107–109 | C | C | C | C | B | — |
| 4-(ethyl-carbamoyloximino)-1,3-oxathiolane | 41–43 | A | B | B | C | A | — |
| 4-(N-acetyl-N-ethylcarbamoyl-oximino)-5-methyl-1,3-oxathiolane | 67–68 | A | C | C | C | C | — |
| 4-(N-trichloro-methanesulfenyl-N-methyl-carbamoyloximino)-1,3-oxathiolane | 98–99 | A | B | B | A | A | — |

* IR - (Neat): VS(2.88), VS(3.00), W(3.35), W(3.41), W(3.49), (VS-b(5.78), S(6.20), S(6.35), W(6.91), VS-b(7.2–7.5), S(7.63), M(8.00), M(8.60), M(8.69), S(9.00), S(9.36), M(9.65), S-b(9.9–10.2), VS-b(10.4–11.0), W(11.3, 11.61, 13.00, 13.41), S-b(13.95).
** IR - (Neat): S(2.91), S(3.31), S(3.39), VS-b(5.5–5.9), W(6.0), VS(6.52), M(6.85, 7.00), S(7.21), VS(7.41), VS-b(8.0), S(8.48), S(8.68), S-b(9.0–9.6), VS-b(10.6), M(10.95), S(11.75), S(12.76), M-b(13.05).
*** IR - (Neat): M(3.00), M(3.40), VS(5.75), M(6.19), S(6.61), M(6.90, 7.05, 7.25), W(7.50, 7.66), S-b(7.9–8.1), M(8.50), M(8.76), M-b(8.8–9.4), W(9.78, 9.98), VS(10.56), S(10.80), W(11.6, 11.8, 13.10).
**** IR - (Neat): M(2.98), W(3.71), M(3.83, 3.40), VS-b(5.6–6.0), S(6.18), VS-b(6.5–6.8), S(6.90), S(7.22), S-b(7.7–8.3), S(8.5–8.9), S(9.3), S(10.05), VS-b(10.5–11.0), M(11.55–11.87), M-b(13.1–14.2).
VS = Very strong; S = strong; M = medium; W = weak, b = broad; only prominent and/or diagnostic bands are noted.

At higher dosage rates all of the above compositions may be expected to exhibit some activity against the various test species, however the data presented in Table I above clearly indicates a rather high degree of selectivity for some compositions and a broad spectrum of activity for others.

It will be understood that the insect species employed in the above tests are merely representative of a wide variety of pests that can be controlled by use of our compounds. These compounds demonstrate systemic as well as contact toxicity against insects and mites.

It should be noted that in addition to their insecticidal and miticidal activity, noteworthy nematocidal activity was also displayed by our compounds.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredients is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 per cent by weight and in the solid formulations from about 0.5 to about 90 per cent by weight. Satisfactory sprays, dusts, or granules for general use contain from about ¼ to 15 pounds of active toxicant per acre.

The pesticides contemplated herein prevent attack by insects, mites and nematodes upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

What is claimed is:

1. A pesticide composition comprising an acceptable carrier and an effective, insecticidal, miticidal or nematocidal amount of a compound of the formula:

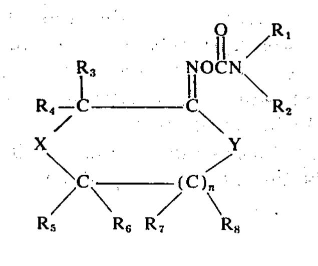

wherein:

$R_1$ and $R_2$ may be the same or different and may be hydrogen, lower alkyl, halogen substituted lower alkyl, cycloalkyl, lower alkoxyalkyl, lower alkylthioalkyl, lower alkylsulfinylalkyl, lower alkylsulfonylalkyl, lower alkenyl, lower alkynyl, aryl, aryl substituted with one or more halogen, lower alkyl or lower alkoxy substituents, lower alkanoyl, alkoxy or halogen substituted lower alkanesulfenyl with the proviso that when $R_1$ is lower alkoxy, lower alkanoyl or halogen substituted with alkanesulfenyl, $R_2$ is hydrogen, lower alkyl or halogen substituted lower alkyl;

$R_3$, $R_4$, $R_5$, $R_6$, $R_7$ and $R_8$ may be the same or different and may be hydrogen, alkyl, alkenyl, alkoxyalkyl, alkylthioalkyl, alkylsulfinylalkyl or alkylsulfonylalkyl, with the proviso that no one of said substituent groups may contain more than six carbon atoms;

X and Y may be O, S, SO or $SO_2$ with the proviso that X or Y is O and when X is O, Y is other than O and when Y is O, X is other than O; and

*n* is 0 or 1.

2. A composition as claimed in claim 1 wherein X is O and Y is S,SO or $SO_2$.

3. A composition as claimed in claim 1 wherein Y is O and X is S, SO or $SO_2$.

4. A composition as claimed in claim 1 wherein *n* is 0.

5. A composition as claimed in claim 1 wherein *n* is 1.

6. A composition as claimed in claim 1 wherein $R_1$ is hydrogen and $R_2$ is methyl.

7. A composition as claimed in claim 1 wherein $R_1$ is methyl and $R_2$ is trihalomethanesulfenyl.

8. A composition as claimed in claim 1 wherein X is S, Y is O, *n* is 1 and $R_3$, $R_4$, $R_5$, $R_6$, $R_7$and $R_8$ are individually hydrogen or alkyl.

9. A composition as claimed in claim 8 wherein $R_1$ is hydrogen or methyl and $R_2$ is methyl or trihalomethanesulfenyl.

10. A composition as claimed in claim 1 wherein X is O, Y is S, and $R_3$, $R_4$, $R_5$, $R_6$, $R_7$ and $R_8$ are individually hydrogen or alkyl.

11. A composition as claimed in claim 10 wherein $R_1$ is hydrogen or methyl and $R_2$ is methyl or trihalomethanesulfenyl.

12. The composition according to claim 1 wherein said compound is 4-(methylcarbamoyloximino)-5-ethyl-1,3-oxathiolane.

13. The composition according to claim 1 wherein said compound is 4-(N-methyl-N-trichloromethanesulfenylcarbamoyloximino)-5-methyl-1,3-oxathiolane.

14. The composition according to claim 1 wherein said compound is 2-(N-methyl-N-trichloromethanesulfenylcarbamoyloximino)-3,3-dimethyl-1,4-oxathiane.

15. A method of controlling insects, mites and nematodes which comprises subjecting them to an effective insecticidal, miticidal or nematocidal amount of a compound of the formula:

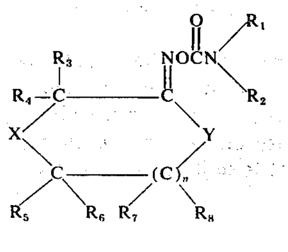

wherein:

$R_1$ and $R_2$ may be the same or different and may be hydrogen, lower alkyl, halogen substituted lower alkyl, cycloalkyl, lower alkoxyalkyl, lower alkylthioalkyl, lower alkylsulfinylalkyl, lower alkylsulfonylalkyl, lower alkenyl, lower alkynyl, aryl, aryl substituted with one or more halogen, lower alkyl or lower alkoxy substituents, lower alkanoyl, alkoxy or halogen substituted lower alkanesulfenyl with the proviso that when $R_1$ is lower alkoxy, lower alkanoyl or halogen substituted lower alkanesulfenyl, $R_2$ is hydrogen, lower alkyl or halogen substituted lower alkyl;

$R_3$, $R_4$, $R_5$, $R_6$, $R_7$ and $R_8$ may be the same or different and may be hydrogen, alkyl, alkenyl, alkoxyalkyl, alkylthioalkyl, alkylsulfinylalkyl or alkylsulfonylalkyl, with the proviso that no one of said substituent groups may contain more than six carbon atoms;

X and Y may be O, S, SO or $SO_2$ with the proviso that X or Y is O and when X is O, Y is other than O and when Y is O, X is other than O; and

*n* is 0 or 1.

16. The method as claimed in claim 15 wherein X is O and Y is S, SO or $SO_2$.

17. The method as claimed in claim 15 wherein Y is O and X is S, SO or $SO_2$.

18. The method as claimed in claim 15 wherein *n* is 0.

19. The method as claimed in claim 15 wherein *n* is 1.

20. The method as claimed in claim 15 wherein $R_1$ is hydrogen and $R_2$is methyl.

21. The method as claimed in claim 15 wherein $R_1$ is methyl and $R_2$ is trihalomethanesulfenyl.

22. The method as claimed in claim 15 wherein X is S, Y is O, *n* is 1 and $R_3$, $R_4$, $R_5$, $R_6$, $R_7$ and $R_8$ are individually hydrogen or alkyl.

23. The method as claimed in claim 15 wherein $R_1$ is hydrogen or methyl and $R_2$ is methyl or trihalomethanesulfenyl.

24. The method as claimed in claim 15 wherein X is O, Y is S, and $R_3$, $R_4$, $R_5$, $R_6$, $R_7$ and $R_8$ are individually hydrogen or alkyl.

25. The method as claimed in claim 15 wherein $R_1$ is hydrogen or methyl and $R_2$ is methyl or trihalomethanesulfenyl.

26. The method as claimed in claim 15 wherein said compound is 4-(methylcarbamoyloximino)-5-ethyl-1,3-oxathiolane.

27. The method as claimed in claim 15 wherein said compound is 4-(N-methyl-N-trichloromethanesulfenyl-carbamoyloximino)-5-methyl-1,3-oxathiolane.

28. The method as claimed in claim 15 wherein said compound is 2-(N-methyl-N-trichloromethanesulfenyl-carbamoyloximino)-3,3-dimethyl-1,4-oxathiane.

* * * * *

UNITED STATES PATENT OFFICE

CERTIFICATE OF CORRECTION

Patent No. 3,956,500 Dated May 11, 1976

Inventor(s) John A. Durden et al. Page 1 of 2

It is certified that error appears in the above-identified patent and that said Letters Patent are hereby corrected as shown below:

Col. 4, lines 21 through 25

"

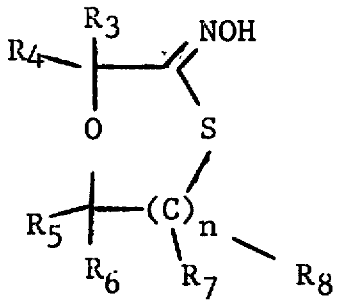

" should read

"

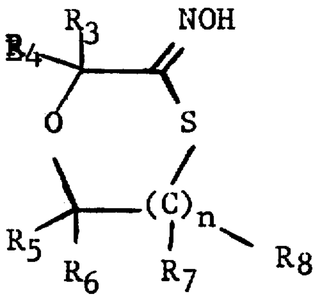

"

UNITED STATES PATENT OFFICE
CERTIFICATE OF CORRECTION

Patent No. 3,956,500 Dated May 11, 1976

Inventor(s) John A. Durden et al. Page 2 of 2

It is certified that error appears in the above-identified patent and that said Letters Patent are hereby corrected as shown below:

Col. 8, line 58 "C, 35,55" should read "C, 35.55".

Col. 9, line 10 "rimethylchlorosilane" should read "trimethylchlorosilane".

Col. 9, line 18 after the word "pure" omit "90.5°" and insert -- oxime --.

Col. 9, line 19 "89.0° - 5°C" should read "89.0° - 90.5°C".

Col. 16, line 60 "emperature" should read "temperature".

Col. 23, line 21 "ingredients" should read -- ingredient --.

Signed and Sealed this

Twenty-first Day of December 1976

[SEAL]

*Attest:*

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 3,956,500 Dated May 11, 1976

Inventor(s) John A. Durden et al.

It is certified that error appears in the above-identified patent and that said Letters Patent are hereby corrected as shown below:

Column 19, lines 1 to 3 which reads:

"A = no control
B = partial control
C = excellent control"

should read:

"A = excellent control
B = partial control
C = no control".

Signed and Sealed this

*Sixth* Day of *December 1977*

[SEAL]

*Attest:*

RUTH C. MASON
*Attesting Officer*

LUTRELLE F. PARKER
*Acting Commissioner of Patents and Trademarks*